(12) United States Patent
Dlubala et al.

(10) Patent No.: US 8,461,122 B2
(45) Date of Patent: Jun. 11, 2013

(54) DERIVATIVES OF MORPHINE-6-GLUCURONIDE, PREPARATION METHOD THEREOF AND USE OF SAME IN THERAPEUTICS

(75) Inventors: Alain Dlubala, Paris (FR); Claire Trecant, Strasbourg (FR); Isabelle Ripoche, Aubiere Cedex (FR)

(73) Assignee: Sanofi, Paris (FR)

( * ) Notice: Subject to any disclaimer, the term of this patent is extended or adjusted under 35 U.S.C. 154(b) by 92 days.

(21) Appl. No.: 13/155,655

(22) Filed: Jun. 8, 2011

(65) Prior Publication Data

US 2011/0301107 A1 Dec. 8, 2011

Related U.S. Application Data

(63) Continuation of application No. PCT/FR2009/052448, filed on Dec. 8, 2009.

(30) Foreign Application Priority Data

Dec. 10, 2008 (FR) ..................... 08 06949

(51) Int. Cl.
| | | |
|---|---|---|
| *A01N 43/04* | (2006.01) | |
| *A01N 43/42* | (2006.01) | |
| *A61K 31/70* | (2006.01) | |
| *A61K 31/44* | (2006.01) | |
| *C07D 489/00* | (2006.01) | |
| *C07H 15/00* | (2006.01) | |
| *C07H 17/00* | (2006.01) | |
| *C07H 17/02* | (2006.01) | |

(52) U.S. Cl.
USPC ........... 514/33; 514/282; 536/17.3; 536/17.4; 536/17.9; 536/18.1; 546/44

(58) Field of Classification Search
None
See application file for complete search history.

(56) References Cited

U.S. PATENT DOCUMENTS

| 3,766,188 A | 10/1973 | Murakami et al. |
| 2007/0116665 A1 | 5/2007 | Temsamani et al. |

FOREIGN PATENT DOCUMENTS

| FR | 2864082 | 6/2005 |
| WO | WO 93/03051 | 2/1993 |
| WO | WO 95/05831 | 3/1995 |
| WO | WO 98/46618 | 10/1998 |
| WO | WO 99/64430 | 12/1999 |
| WO | WO 2005/063263 | 7/2005 |

OTHER PUBLICATIONS

Hu et al., Acta Anaesthesiol Sin. Dec. 2000;38(4): abstract.*
U.S. Appl. No. 13/155,646, filed Jun. 8, 2011, Dlubala, et al.
U.S. Appl. No. 13/155,727, filed Jun. 8, 2011, Dlubala, et al.
Yoshimura, H., et al., Metabolism of Drugs, LX. 1) The Synthesis of Codeine and Morphine Glucuronides 2), Chem. Pharm. Bull. vol. 16, No. 11, pp. 2114-2119, (1968).
Abdel-Monem, M. M., et al., N-Demethylation of Morphine and Structurally Related Compounds With Chloroformate Esters, Journal of Medicinal Chemistry, vol. 15, No. 2, (1972), pp. 208-210.
Auterhoff et al., Die Farbreaktion des Morphins Nach E. Marquis, Archiv Der Parmazie (Weinheim), vol. 306, No. 11,(1973), pp. 866-872.
Berrang, B., et al., Synthesis of Morphine-3,6-di-B-D-Glucuronide, Synthesis, (1997), pp. 1165-1168.
Brown, R. T., et al., A Simple Synthesis of Morphine-3,6-di-B-D-Glucuronide, Tetrahedron, vol. 56, (2000), pp. 7591-7594.
Cheng, G., et al., Syn Additions to 4a-Epoxypyranosides: Synthesis of L-Idopyranosides, Organic Letters, vol. 9, No. 23, pp. 4849-4852. (2007).
D'Amour, et al., A Method for Determining Loss of Pain Sensation, Journal of Pharmacology and Exp. Ther., vol. 72, pp. 74-79, (1941).
Danishefsky, S. J., et al., A Stereoselective Totally Synthetic Route to Methyl a-Peracetylhikosaminide, J. Am. Chem. Soc., (1989), vol. 111, pp. 2193-2204.
Frances, B., et al., Further Evidence That Morphine-6B-Glucuronide is a More Potent Opioid Agonist Than Morphins, The Journal of Pharmacology and Experimental Therapeutics, vol. 262, No. 1, pp. 25-31, (1992).
Frensch, K., et al., Notiz Uber Oligoethylenglykolether des Morphins, Liebigs Ann. Chem. (1979), pp. 2118-2120.
McMillan, K. G., et al., Synthesis, Structure and Reactivity of 5-Pyranosyl-1,3,4-Oxathiazol-2-Ones, Carbohydrate Research, vol. 341, (2006). pp. 41-48.

(Continued)

*Primary Examiner* — Traviss C McIntosh, III
(74) *Attorney, Agent, or Firm* — Robert Kajubi; Ronald G. Ort

(57) ABSTRACT

The disclosure relates to derivatives of morphine-6-glucuronide of formula (I)

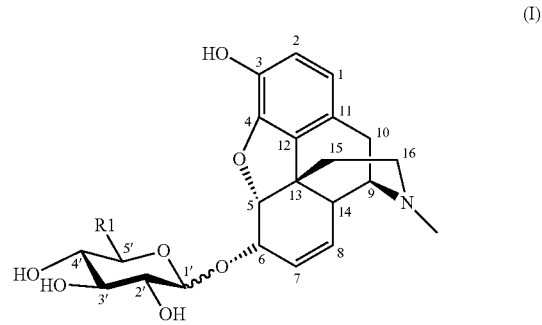

(I)

wherein R1 is as defined in the disclosure, or an acid addition salt thereof, as well as in hydrate or solvate form. The disclosure also relates to the preparation method thereof and to the use of same in therapeutics.

18 Claims, No Drawings

OTHER PUBLICATIONS

Nakajima, R., et al., Synthesis of Methyl 1-O-(4-Hydroxymethamphetminyl)-a-D-Glucopyranouronate, Chem. Pharm. Bull., vol. 53, No. 6, pp. 684-687, (2005).

Narita, M., et al., Regulations of Opioid Dependence by Opioid Receptor Types, Pharmacology & Therapeutics, vol. 89, (2001), pp. 1-15.

Paul, D., et al., Pharmacological Characterization of Morphine-6B-Glucuronide, A Very Potent Morphine Metabolite, The Journal of Pharmacology and Experimental Therapeutics, (1989), vol. 251, pp. 477-483.

Vlahov, J., et al., Uber Eine Verbesserte Synthese Von B-Glucosiduronsaure-Derivaten, Liebigs Ann. Chem., (1983), pp. 570-574.

International Search Report for WO2010/067010 dated Jun. 17, 2010.

* cited by examiner

DERIVATIVES OF MORPHINE-6-GLUCURONIDE, PREPARATION METHOD THEREOF AND USE OF SAME IN THERAPEUTICS

This application is a continuation of International application No. PCT/FR2009/052448, filed Dec. 8, 2009, which is incorporated herein by reference in its entirety; which claims the benefit of priority of French Patent Application No. 0806949, filed Dec. 10, 2008.

FIELD OF THE INVENTION

The present invention relates to morphine-6-glucuronide derivatives, to their preparation and to their use for treating and preventing pain.

One subject of the present invention is compounds corresponding to formula (I)

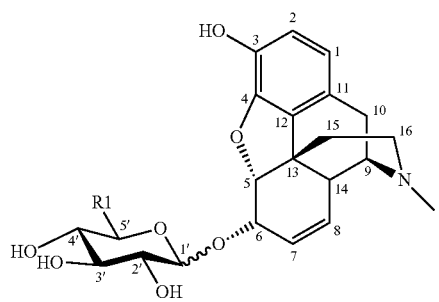

in which:

R1 is a 5-membered heteroaromatic group optionally substituted with one or more substituents chosen from halogen atoms and groups ($C_1$-$C_4$)alkyl, halogen, hydroxyl, oxo, halo($C_1$-$C_4$)alkyl, halo($C_1$-$C_4$)alkyloxy, ($C_1$-$C_4$)alkyloxy, aryl ($C_1$-$C_4$)alkyl and aryl, the said aryl group being optionally substituted with one or more groups chosen from the groups ($C_1$-$C_4$)alkyl, halo($C_1$-$C_4$)alkyl, hydroxyl and ($C_1$-$C_4$)alkyloxy, in the form of base or of an acid-addition salt, and also in the form of a hydrate or a solvate.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) comprise an anomeric carbon. They may exist in the form of α or β anomers. The α and β anomers and the mixture thereof form part of the invention.

The compounds of formula (II) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I), also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:

a halogen atom: a fluorine, chlorine, bromine or iodine atom;

a ($C_1$-$C_4$)alkyl group: a substituted or unsubstituted, linear or branched, saturated aliphatic group containing between 1 and 4 carbon atoms; examples that may be mentioned include methyl, ethyl, propyl, isopropyl, butyl, isobutyl and tert-butyl groups;

a halo($C_1$-$C_4$)alkyl group: an alkyl group in which one or more hydrogen atoms have been replaced with a halogen atom as defined above; examples of halo($C_1$-$C_4$)alkyl groups that may be mentioned in particular include fluoromethyl, difluoromethyl, trifluoromethyl, chloromethyl, dichloromethyl, trichloromethyl, fluoroethyl, difluoroethyl, trifluoroethyl, chloroethyl, dichloroethyl and trichloroethyl groups;

a hydroxyl group: an —OH group;

an oxo group: group =O a group ($C_1$-$C_4$)alkyloxy: a group —O—($C_1$-$C_4$)alkyl in which the group ($C_1$-$C_4$)alkyl is as defined previously; examples that may be mentioned include methoxy, ethoxy, propoxy and butyloxy groups;

a group halo($C_1$-$C_4$)alkyloxy: a group ($C_1$-$C_4$)alkyloxy in which one or more hydrogen atoms have been replaced with a halogen atom as defined above; examples that may be mentioned include the groups —$OCF_3$, —$OCHF_2$ and —$OCCl_3$;

an aryl group: a substituted or unsubstituted cyclic aromatic group containing between 5 and 14 carbon atoms; examples of unsubstituted aryl groups that may be mentioned include phenyl and naphthyl groups; examples of substituted aryl groups that may be mentioned include groups ($C_1$-$C_4$)alkyloxyphenyl such as methoxyphenyl, ethoxyphenyl, propoxyphenyl and butyloxyphenyl groups;

a group aryl($C_1$-$C_4$)alkyl: an alkyl group in which one or more hydrogen atoms have been replaced with an aryl group; an example that may be mentioned is the benzyl group;

a 5-membered heteroaromatic heterocyclic group: a cyclic aromatic group containing from 1 to 4 carbon atoms and comprising one or more heteroatoms, such as nitrogen, oxygen or sulfur; examples of 5-membered heteroaromatic heterocyclic groups that may be mentioned include pyrrolyl, furyl, thiophenyl, pyrazolyl, imidazolyl, triazolyl, tetrazolyl, oxazolyl, isoxazolyl, oxadiazolyl, thiazolyl, isothiazolyl and thiadiazolyl groups.

Among the compounds of formula (I) that are subjects of the invention, a first group of compounds has one or more of the following characteristics:

the heteroaromatic heterocyclic group is chosen from pyrrole, furan, thiophene, imidazole, triazole, tetrazole, oxazole, isoxazole, oxadiazole, thiazole, isothiazole and thiadiazole groups, and when the heteroaromatic heterocyclic group is substituted with one or more groups, the said group is chosen from methyl, ethyl, propyl, isopropyl, butyl, isobutyl, tert-butyl, fluoromethyl, difluoromethyl, trifluoromethyl, chloromethyl, dichloromethyl, trichloromethyl, fluoroethyl, difluoroethyl, trifluoroethyl, chloroethyl, dichloroethyl, trichloroethyl, methoxyphenyl, ethoxyphenyl, propoxyphenyl and butyloxyphenyl groups.

Among the compounds mentioned previously, mention may be made in particular of the compounds of formula (I) for which:

the heteroaromatic heterocyclic group is chosen from tetrazole, triazole, in particular 1,2,4-triazole, and oxadiazole, in particular 1,3,4-oxadiazole groups, and when the heteroaromatic heterocyclic group is substituted with at least one group, the said group is chosen from methyl, trifluoroethyl and p-methoxyphenyl groups.

Among the compounds of formula (I) that are subjects of the invention, mention may be made especially of the following compounds:

morphin-6-yl 5-C-(tetrazol-5-yl)α/β-D-xylopyranoside (1/1)

morphin-6-yl 5-C-(tetrazol-5-yl)-β-D-xylopyranoside morphin-6-yl 5-C-(2-methyl-1,3,4-oxadiazol-5-yl)α/β-D-xylopyranoside (2/3)

morphin-6-yl 5-C-(2-methyl-1,3,4-oxadiazol-5-yl)-α-D-xylopyranoside morphin-6-yl 5-C-(2-methyl-1,3,4-oxadiazol-5-yl)-β-D-xylopyranoside and morphin-6-yl 5-C-[5-(4-methoxyphenyl)-4-(2,2,2-trifluoroethyl)-4H-1,2,4-triazol-3-yl]-β-D-xylopyranoside.

Preparation Process

In the text hereinbelow, the term "protecting group PG" means a group that can, firstly, protect a reactive function such as a hydroxyl or an amine during a synthesis, and that can, secondly, enable regeneration of the intact reactive function at the end of the synthesis. Examples of protecting groups and of protection and deprotection methods are given in "Protective Groups in Organic Synthesis" Greene et al., 2$^{nd}$ Edition (John Wiley & Sons, Inc., New York).

In the text hereinbelow, the term "leaving group LG" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, 3$^{rd}$ Edition, Wiley Interscience, pp. 310-316.

In accordance with the invention, the compounds of general formula (I) may be prepared according to the following process illustrated by Scheme 1.

Scheme 1

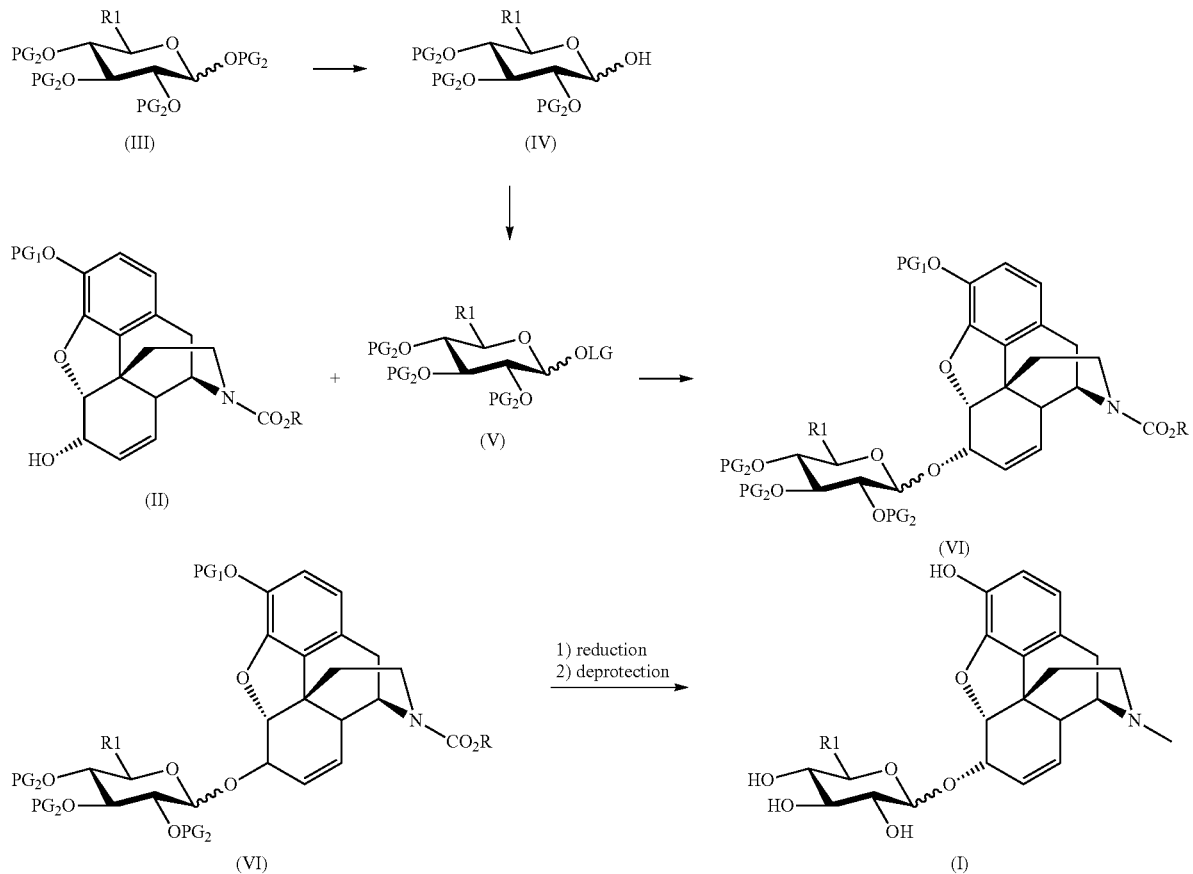

In a first step, a compound of general formula (II), in which $PG_1$ represents a protecting group such as a pivaloyl group and R represents a ($C_1$-$C_4$)alkyl group, for example a methyl or an ethyl, may be coupled to a compound of general formula (V), in which R1 is as defined in the general formula (I), $PG_2$ is a protecting group such as a benzoyl group and LG is an activating group such as a trichloroacetimidate group —CNHCCl$_3$, to obtain a compound of general formula (VI).

The coupling reaction may be performed, for example, in the presence of a Lewis acid, such as trimethylsilyl trifluoromethanesulfonate (TMSOTf), in a solvent such as dichloromethane, at a temperature of between 0° C. and 25° C.

In certain cases, the compound of general formula (V) may be protected prior to the coupling reaction. For example, when R1 represents a tetrazolyl group, it may be protected beforehand with a protecting group such as a 4-methoxybenzyl group. After the coupling reaction, this protecting group may be cleaved off, for example in the case of a tetrazolyl group bearing a 4-methoxybenzyl group, in the presence of trifluoroacetic acid (TFA) at the reflux temperature.

The compound of general formula (II) may be prepared, for example, according to the method described in Portoghese et al., *J. Med. Chem.* 1972, 15, 208-210.

The compound of general formula (V) may be obtained by activating the hydroxyl function of the compound of general formula (IV), in which R1 and PG2 are as defined above. When the group LG is a leaving group such as a trichloroacetimidate group —CNHCCl$_3$, the reaction may be performed in the presence of trichloroacetonitrile and a strong base such as 1,8-diazabicyclo[5.4.0]undec-7-ene, in a solvent such as dichloromethane.

The compound of general formula (IV) may be obtained beforehand by anomeric deprotection of the compound of general formula (III) in which R1 and PG2 are as defined above. When PG2 represents a benzoyl group, deprotection of the hydroxyl group may be performed in the presence of hydrazine hydrate (NH$_2$NH$_2$, CH$_3$COOH).

In a second step, the compound of general formula (VI) is reduced and deprotected simultaneously, for example in the presence of lithium aluminium hydride, in a solvent such as tetrahydrofuran, at the reflux temperature of the reaction medium, and is then isolated in the presence of a mineral acid such as hydrochloric acid. The compound of general formula (I) is thus obtained.

When R1 represents a 2-methyl-1,3,4-oxadiazol-5-yl group, the compound of general formula (I) may be obtained from the corresponding compound of general formula (I) for which R1 represents a tetrazolyl group, this group being prepared according to the method illustrated in Scheme 2.

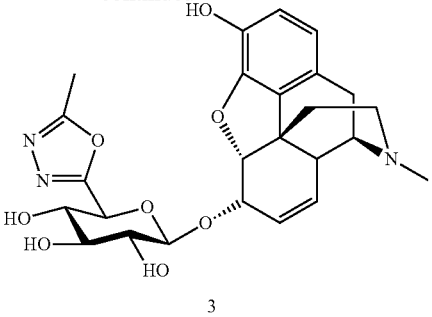

According to Scheme 2 and in a first step, morphin-6-yl 5-C-(tetrazol-5-yl)-β-D-xylopyranoside (1) can react with an acyl chloride or an acid anhydride, such as acetic anhydride, according to a Huisgen thermal rearrangement, to give 3-O-acetylmorphin-6-yl 2,3,4-tri-O-acetyl-5-C-(2-methyl-1,3,4-oxadiazol-5-yl)-β-D-xylopyranoside (2). In a second step, the hydroxyl groups are deprotected, for example in the presence of sodium methoxide, to give morphin-6-yl 5-C-(2-methyl-1,3,4-oxadiazol-5-yl)-β-D-xylopyranoside (3).

In Schemes 1 and 2, the starting compounds and the reagents, when their mode of preparation is not described, are commercially available or described in the literature, or may be prepared according to methods that are described therein or that are known to those skilled in the art.

Synthetic Intermediates

According to another of its aspects, a subject of the invention is also the compounds of general formulae (III), (IV) and (V). These compounds are useful as intermediates for the synthesis of the compounds of general formula (I).

A subject of the invention is, more particularly, the compounds of formulae (IIIa), (IIIb), (IIIc), (IVb), (IVc), (Vb) and (Vc).

Compounds (IIIb), (IVb) and (Vb) exist in the form of a mixture of the two positional isomers of the para-methoxybenzyl (PMB) group.

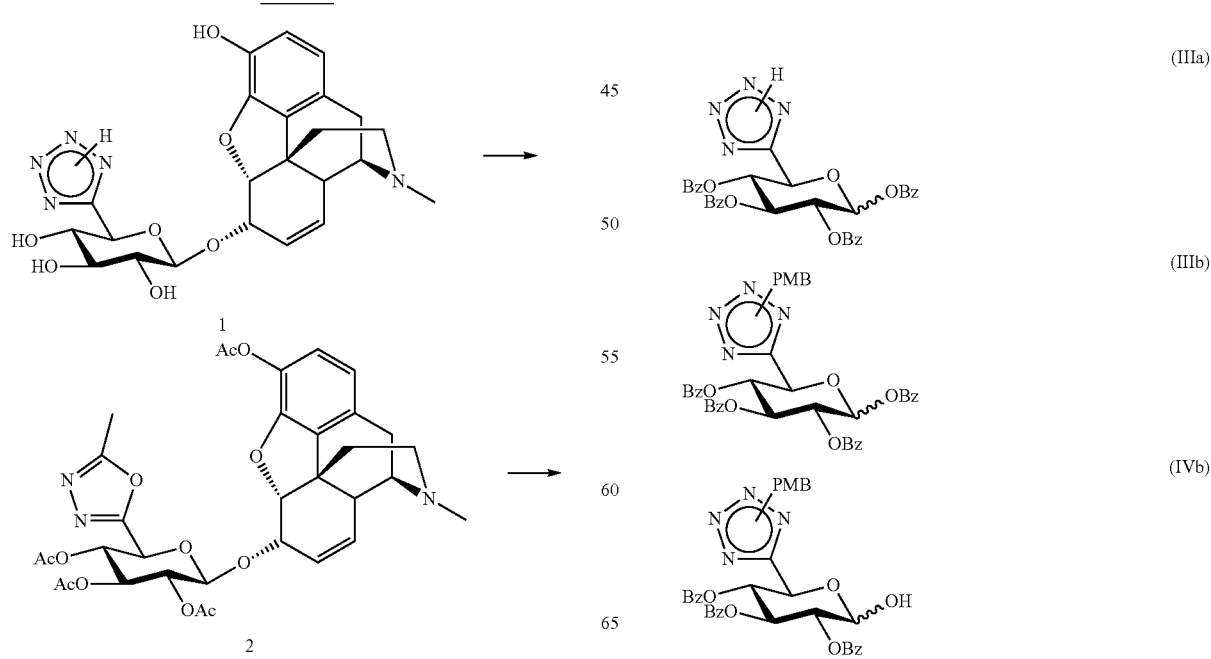

-continued
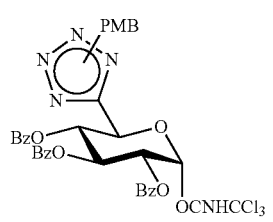
(Vb)
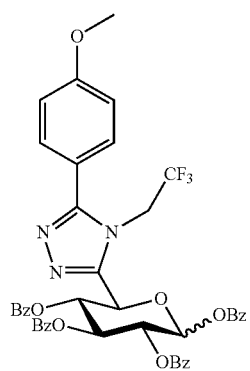
(IVc)
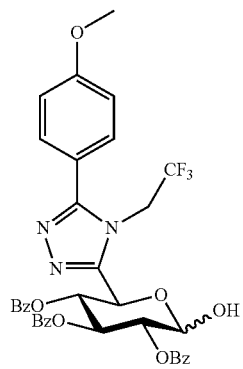
(Vc)
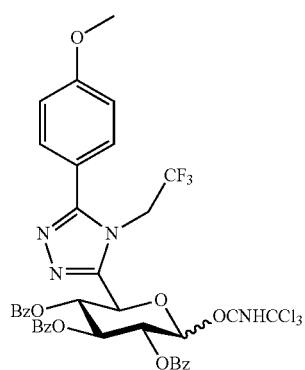
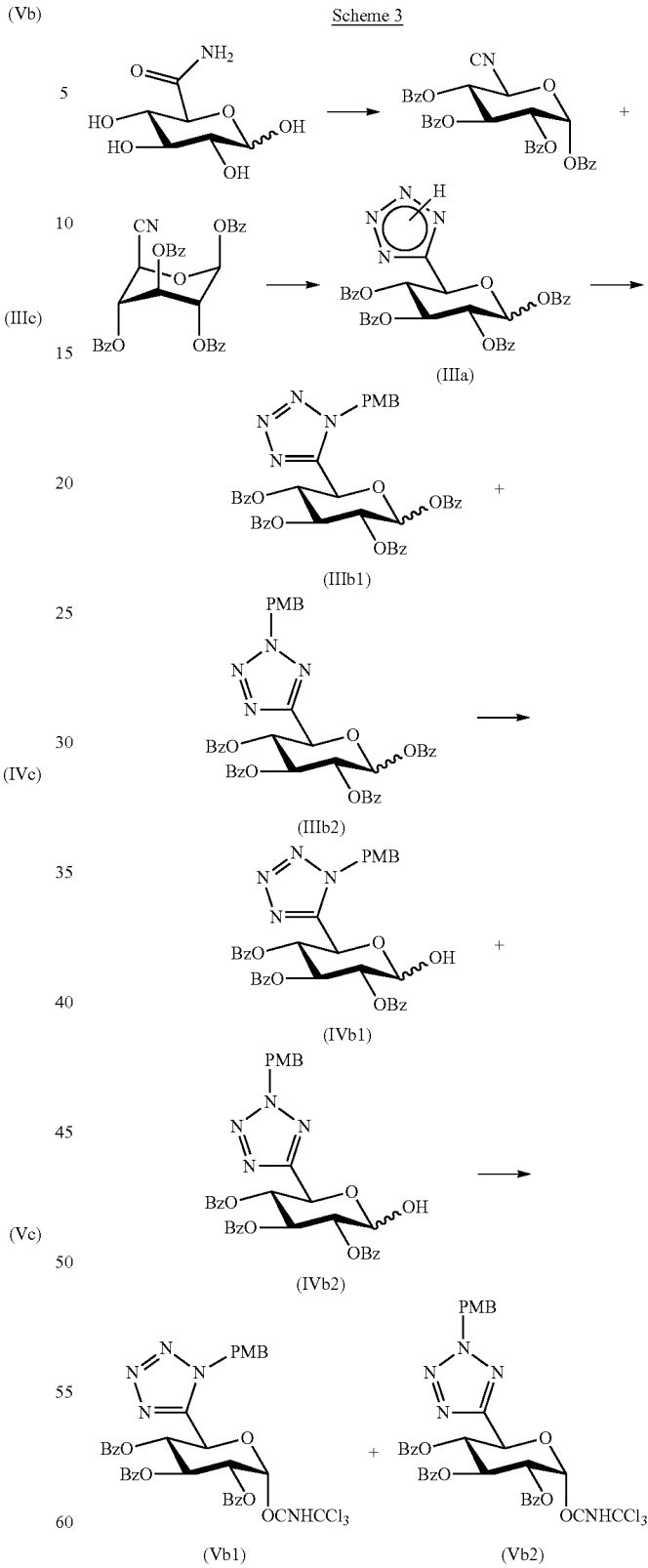
The compounds of formulae (IIIa), (IIIb), (IVb) and (Vb) may be obtained according to the method described in Scheme 3.
In Scheme 3, the compound of formula (IIIa) protected, for example, with benzoate groups may be obtained by protection, dehydration and then tetrazolylation of D-glucuronamide. One tetrazolylation method consists in reacting the nitrile function in refluxing toluene in the presence of trimethylsilyl azide (TMSN$_3$) and bis(tributyltin) oxide (Bu$_3$Sn)$_2$O. As regards the D-glucuronamide protection reaction, an adaptation of the method described in Carbohydrate Research 2006, 341, 1, 41-48 may be used.

The compound of formula (IIIb), consisting of a mixture of compounds (IIIb1) and (IIIb2), may be obtained from the compound of formula (IIIa) via protection of the amine, for example with a para-methoxybenzyl group.

Selective deprotection of the anomeric position of the compound of formula (IIIb) makes it possible to obtain the compound of formula (IVb), consisting of a mixture of compounds (IVb1) and (IVb2). In the case of a protecting group of benzoate type, this deprotection may be performed in the presence of hydrazine acetate.

The free hydroxyl function of the compound of formula (IVb) may be converted into an imidate to generate the compound of formula (Vb), consisting of a mixture of compounds (Vb1) and (Vb2). Transformation of the hydroxyl function into an imidate function may be performed, for example, in the presence of trichloroacetonitrile and DBU (1,8-diazabicyclo[5.4.0]undec-7-ene) according to an adaptation of the method described in Tetrahedron 2000, 56, 7591-7594.

The compounds of formulae (IIIc), (IVc) and (Vc) may be obtained according to the method described in Scheme 4.

Scheme 4

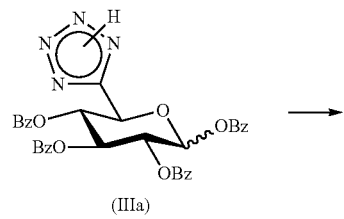

(IIIa)

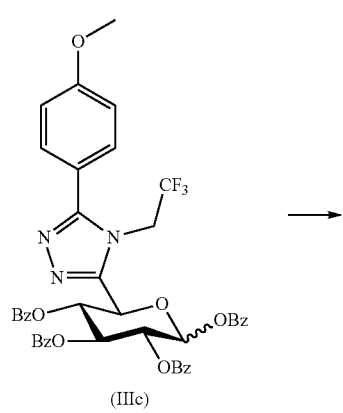

(IIIc)

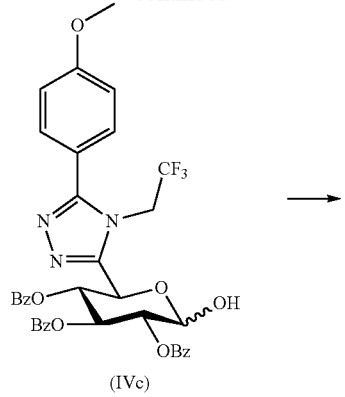

(IVc)

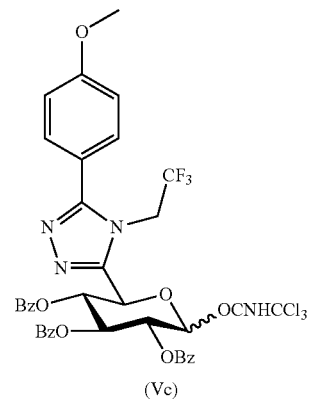

(Vc)

According to Scheme 4, the compound of formula (IIIa) described above may undergo a Huisgen thermal rearrangement in the presence of an imidoyl chloride, for example 2,2,2-trifluoro-N-(4-methoxybenzyl)acetimidoyl chloride, to give the compound of formula (IIIc).

Selective deprotection of the anomeric position of the compound of formula (IIIc) makes it possible to obtain the compound of formula (IVc). In the case of a protecting group of benzoate type, this deprotection may be performed in the presence of hydrazine hydrate.

The free hydroxyl function of the compound of formula (IVc) may be converted into an imidate to generate the compound of formula (Vc). The transformation of the hydroxyl function into an imidate function may be performed, for example, in the presence of trichloroacetonitrile and DBU (1,8-diazabicyclo[5.4.0]undec-7-ene) according to an adaptation of the method described in Tetrahedron 2000, 56, 7591-7594.

The invention is illustrated in a non-limiting manner by the examples below.

The examples that follow describe the preparation of certain compounds in accordance with the invention. These examples are not limiting, and serve merely to illustrate the present invention. The numbers of the compounds presented as examples refer to those given in the table hereinbelow, which illustrates the chemical structures and the physical properties of a number of compounds according to the invention.

EXAMPLES

Example 1

Morphin-6-yl 5-C-(tetrazol-5-yl)-β-d-xylopyranoside trifluoroacetate (Compound 2)

1.1. 1,2,3,4-tetra-O-benzoyl-α/β-D-glucurononitrile

To a suspension of D-glucuronamide (25.0 g, 0.129 mol) in pyridine (100 mL) at room temperature is added over 30 minutes a solution of benzoyl chloride (102 mL, 0.878 mol) in dichloromethane (90 mL). The reaction medium is stirred overnight at room temperature, and dichloromethane (200 mL) and water (200 mL) are then added. The organic phase is washed with 1N hydrochloric acid solution (200 mL), saturated sodium hydrogen carbonate solution (3×200 mL) and saturated sodium chloride solution (200 mL). The organic phase is dried over sodium sulfate and the solvent is removed under reduced pressure. The residue (yellow oil) is triturated in ethanol (200 mL) to give a mixture of anomers (43.4 g, 57%) in the form of pale yellow crystals. The proton NMR spectrum in deuteriochloroform, $CDCl_3$, shows a ratio α:β of 2:1.

Melting point: 209-212° C.

$^1H$ NMR (400 MHz, $CDCl_3$): δ 8.10-7.30 (m, 20Hα+20Hβ, H-aro), 6.88 (d, 1Hα, J 3.5 Hz, H-1α), 6.57 (d, 1Hβ, J 3.0 Hz, H-1β), 6.21 (t, 1Hα, J 9.5 Hz, H-3α), 5.93 (t, 1Hα, J 9.5 Hz, H-4α), 5.84 (t, 1Hβ, J 4.0 Hz, H-3β), 5.71-5.65 (m, 1Hα 1Hβ, H-2α, H-4β), 5.64 (m, 1Hβ, H-2β), 5.16 (d, 1Hβ, J 4.0 Hz, H-5β), 5.11 (d, 1Hα, J 9.5 Hz, H-5α).

$^{13}C$ NMR (100 MHz, $CDCl_3$) δ 165.5, 165.1, 164.8, 164.6, 164.3, 163.8 (C=O), 134.4-128.0 (C-aro), 115.3 (C-6β), 114.1 (C-6α), 90.9 (C-1β), 89.4 (C-1α), 69.3, 69.2, 69.0 (C-2α, C-3α, C-4α), 67.4 (C-4β), 66.7, 66.5 (C-2β, C-3β), 61.9 (C-5α), 60.8 (C-5β).

Mass calculated for $C_{34}H_{25}NO_9Na$ $[M+Na]^+$ 614.1427, found 614.1422.

1.2. 1,2,3,4-tetra-O-benzoyl-5-C-(tetrazol-5-yl)-α/β-D-xylopyranose

To a solution of 1,2,3,4-tetra-O-benzoyl-α/β-D-glucurononitrile prepared beforehand (43.0 g, 72.8 mmol) in toluene (500 mL) are added bis(tributyltin) oxide (3.70 mL, 7.26 mmol) and trimethylsilyl azide (28.7 mL, 216 mmol). The reaction medium is stirred overnight at reflux. The solvent is removed under reduced pressure and the residue is purified by chromatography on silica gel (1:1 to 0:1 cyclohexane/ethyl acetate) to give 1,2,3,4-tetra-O-benzoyl-5-C-(tetrazol-5-yl)-α/β-D-xylopyranose (27.0 g, 59%) in the form of brown crystals. The proton NMR spectrum in $CDCl_3$ shows a ratio α:β of 2:1.

Melting point 144-147° C.

$^1H$ NMR (400 MHz, $CDCl_3$): δ 8.19-7.28 (m, 20Hα+20Hβ, H-aro), 7.06 (d, 1Hα, J 3.5 Hz, H-1α), 6.50-6.44 (m, 1Hβ+1Hα, H-1β, H-3α), 6.21 (t, 1Hβ, J 9.0 Hz, H-3β), 6.13-6.01 (m, 2Hα 1Hα, H-4β, H-4α, H-2β), 5.90-5.85 (m, 2Hα, H-2α, H-5α), 5.66 (d, 1Hβ, J 9.0 Hz, H-5β).

$^{13}C$ NMR (100 MHz, $CDCl_3$) δ 165.79, 165.2, 164.7 (C=O, C=N), 134.4-128.1 (C-aro), 93.0 (C-1β), 89.9 (C-1α), 72.0, 70.5, 70.4, 70.3, 69.5 (C-2α, C-2β, C-3α, C-3β, C-4α, C-4β), 68.9 (C-5β), 67.0 (C-5α).

Mass calculated for $C_{34}H_{26}N_4O_9Na$ $[M+Na]^+$ 657.1597, found 657.1595.

1.3. 1,2,3,4-tetra-O-benzoyl-5-C-[2-(4-methoxybenzyl)-2H-tetrazol-5-yl]-α/β-D-xylopyranose (IIIb2) and 1,2,3,4-tetra-O-benzoyl-5-C-[1-(4-methoxybenzyl)-1H-tetrazol-5-yl]-α/β-D-xylopyranose (IIIb1)

To a solution of 1,2,3,4-tetra-O-benzoyl-5-C-(tetrazol-5-yl)-α/β-D-xylopyranose (21.0 g, 33.12 mmol) in tetrahydrofuran (210 mL) are added triethylamine (5.5 mL, 39.46 mmol) and 4-methoxybenzyl chloride (5.0 mL, 36.71 mmol). The reaction medium is stirred overnight at reflux. The solvent is removed under reduced pressure and the residue purified by chromatography on silica gel (4:1 cyclohexane/ethyl acetate) to give a mixture of isomers (18.5 g, 73%) in the form of pale yellow crystals. The proton NMR spectrum in $CDCl_3$ shows a ratio (IIIb1):(IIIb2) of 2:1 with for (IIIb1) a ratio α/β of 2:1 and for (IIIb2) a ratio α/β of 2:1.

$^1H$ NMR (400 MHz, $CDCl_3$) for the two α anomers: δ 8.21-7.29 (m, 20Ha+20Hb, H-aro), 7.23 (d, 2Hb, J 8.5 Hz, H-aroPMBb), 7.17 (d, 2Ha, J 8.5 Hz, H-aroPMBa), 6.98 (d, 1Ha, J 3.5 Hz, H-1a), 6.96 (d, 1Hb, J 3.5 Hz, H-1b), 6.86 (d, 2Hb, J 8.5 Hz, H-aroPMBb), 6.75 (d, 2Ha, J 8.5 Hz, H-aroPMBa), 6.42 (t, 1Ha, J 10.0 Hz, H-3a), 6.33 (t, 1Hb, J 10.0 Hz, H-3b), 6.13 (t, 1Ha, J 10.0 Hz, H-4a), 5.84 (dd, 1Ha, J 3.5 Hz, J 10.0 Hz, H-2a), 5.76-5.63 (m, 3Ha+5Hb, $CH_2PhOCH_3a$, $CH_2PhOCH_3b$, H-5a, H-2b, H-4b, H-5b), 3.79 (s, 3Hb, $OCH_3b$), 3.75 (s, 3Ha, $OCH_3a$).

$^{13}C$ NMR (100 MHz, $CDCl_3$) for the two α anomers: δ 165.8, 165.2, 164.5, 164.3, 164.2, 162.1 (C=O, C=N), 134.4-124.7 (C-aro), 114.5 (C-aroPMBa), 114.3 (C-aroPMBb), 90.0 (C-1a), 89.7 (C-1b), 71.1 (C-4a), 70.4, 70.2, (C-2a, C-3a), 69.9, 69.6, 69.5 (C-2b, C-3b, C-4b), 67.0 (C-5a), 66.0 (C-5b), 56.7 ($CH_2PhOCH_3a$), 55.3 ($OCH_3b$), 55.2 ($OCH_3a$), 52.1 ($CH_2PhOCH_3b$).

Mass calculated for $C_{42}H_{34}N_4O_{10}Na$ $[M+Na]^+$ 777.2173, found 777.2181.

1.4. 2,3,4-tri-O-benzoyl-5-C-[2-(4-(methoxybenzyl)-2H-tetrazol-5-yl]-α/β-D-xylopyranose (IVb2) and 2,3,4-tri-O-benzoyl-5-C-[1-(4-(methoxybenzyl)-1H-tetrazol-5-yl]-α/β-D-xylopyranose (IVb1))

To a solution of the mixture obtained in step 1.3 (13.4 g, 17.77 mmol) in N,N-dimethylformamide (100 mL) at 0° C. is added hydrazine acetate (2.45 g, 26.60 mmol) portionwise over 15 minutes. The reaction medium is stirred for 1 hour at 0° C. and then for 4 hours at room temperature. The solvent is removed under reduced pressure and the residue purified by chromatography on silica gel (7:3 cyclohexane/ethyl acetate) to give a mixture of isomers of the expected product (8.0 g, 70%) in the form of yellow crystals. The proton NMR spectrum in $CDCl_3$ shows a ratio (IVb2):(IVb1) of 2:1 with for (IVb2) a ratio α/β of 5:1 and for (IVb1) a ratio α/β of 5:1.

$^1H$ NMR (400 MHz, $CDCl_3$) for the two α anomers: δ 8.14-7.15 (m, 17Ha+17Hb, H-aro), 6.96 (d, 2Ha, J 9.0 Hz, H-aroPMBa), 6.71 (d, 2Hb, J 9.0 Hz, H-aroPMBb), 6.36-6.26 (m, 1Ha+1Hb, H-3a, H-3b), 6.02 (t, 1Ha, J 10.0 Hz, H-4a), 5.88 (d, 1Ha, J 3.5 Hz, H-1a), 5.86 (d, 1Hb, J 3.5 Hz, H-1b), 5.85-5.74 (m, 1Ha+3Hb, H-5a, H-5b, $CH_2PhOCH_3b$), 5.63 (s, 2Ha, $CH_2PhOCH_3a$), 5.51-5.42 (m, 1Ha+1Hb, H-4b, H-2a), 5.31 (dd, 1Hb, J 3.5 Hz, J 10.0 Hz, H-2b), 3.82 (s, 3Hb, $OCH_3b$), 3.75 (s, 3Ha, $OCH_3a$).

$^{13}C$ NMR (100 MHz, $CDCl_3$) for the two α anomers: δ165.8, 165.5, 164.7, 162.9, 150.5 (C=O, C=N), 133.7-124.8 (C-aro), 114.5 (C-aroPMBb), 114.2 (C-aroPMBa), 90.9 (C-1a), 90.8 (C-1b), 72.1 (C-2a), 71.8 (C-2b or C-3b or C-4b), 71.2 (C-4a), 70.2 (C-2b or C-3b or C-4b), 70.0 (C-3a), 69.3 (C-2b or C-3b or C-4b), 64.1 (C-5a), 63.4 (C-5b), 56.7

($CH_2PhOCH_3$a), 55.4 ($OCH_3$b), 55.2 ($OCH_3$a), 52.0 Mass calculated for $C_{35}H_{31}N_4O_9$ $[M+H]^+$ 651.2091, found 651.2111.

1.5. 2,3,4-tri-O-benzoyl-5-C-[2-(4-(methoxybenzyl)-2H-tetrazol-5-yl]α-D-xylopyranosyl trichloroacetimidate (Vb2) and 2,3,4-tri-O-benzoyl-5-C-[1-(4-methoxybenzyl)-1H-tetrazol-5-yl]α-D-xylopyranosyl trichloroacetimidate (Vb1)

To a solution of the mixture obtained in step 1.4 (6.0 g, 9.23 mmol) in dichloromethane (170 mL) at room temperature are added 1,8-diazabicyclo[5.4.0]undec-7-ene (278 μL, 1.86 mmol) and then trichloroacetonitrile (14.6 ml, 184 mmol). The reaction medium is stirred for 1 hour at room temperature. A solution of acetic acid (105 μL, 1.83 mmol) in water (50 mL) is added. The phases are separated, the organic phase is washed with water (50 mL) and then dried over sodium sulfate. The solvent is removed under reduced pressure and the residue purified by chromatography on silica gel (silica neutralized beforehand by washing with a 5% solution of triethylamine in ethyl acetate (7:3 cyclohexane/ethyl acetate), to give a mixture of isomers of the expected product (4.7 g, 65%) in the form of yellow crystals. The proton NMR spectrum in $CDCl_3$ shows a ratio (Vb2):(Vb1) of 3:1.

$^1$H NMR (400 MHz, $CDCl_3$): δ 8.77 (s, 1H-b, NHb), 8.69 (s, 1Ha, NHa), 8.20-7.29 (m, 15Ha+17Hb, H-aro), 7.18 (d, 2Ha, J 8.5 Hz, H-aroPMBa), 6.99 (d, 2Hb, J 8.5 Hz, H-aroPMBb), 6.94 (m, 1Ha+1Hb, H-1a, H-1b), 6.74 (d, 2Ha, J 8.5 Hz, H-aroPMBa), 6.36 (t, 1Ha, J 10.0 Hz, H-3a), 6.29 (t, 1Hb, J 10.0 Hz, H-3b), 6.10 (t, 1Ha, J 10.0 Hz, H-4a), 5.80-5.69 (m, 2Ha+3Hb, H-2a, $CH_2PhOCH_3$b, H-5a, H-5b), 5.64 (s, 2Ha, $CH_2PhOCH_3$a), 5.62-5.55 (m, 2Hb, H-4b, H-2b), 3.84 (s, 3Hb, $OCH_3$b), 3.75 (s, 3Ha, $OCH_3$a).

$^{13}$C NMR (100 MHz, $CDCl_3$): δ 165.6, 165.4, 164.4, 162.0, 160.5, 159.9 (C=O, C=N), 134.0-124.8 (C-aro), 114.6 (C-aroPMBb), 114.3 (C-aroPMBa), 93.1 (C-1a), 92.8 (C-1b), 70.9 (C-2b or C-3b or C-4b), 70.7 (C-4a), 70.5 (C-2a), 70.0 (C-2b or C-3b or C-4b), 69.8 (C-3a), 69.3 (C-2b or C-3b or C-4b), 66.9 (C-5a), 66.0 (C-5b), 56.5 ($CH_2PhOCH_3$a), 55.3 ($OCH_3$b), 55.1 ($OCH_3$a), 51.8 ($CH_2PhOCH_3$b).

1.6. 3-O-pivaloyl-N-ethoxycarbonylnormorphin-6-yl 2,3,4-tri-O-benzoyl-5-C-[2-(4-methoxybenzyl)-2H-tetrazol-5-yl]-β-D-xylopyranoside To a solution of the mixture obtained in step 1.5 (3.6 g, 4.54 mmol) and 3-O-pivaloyl-N-ethoxycarbonylnormorphine (1.0 g, 2.34 mmol) in dichloromethane (50 mL) at 0° C. under argon is added trimethylsilyl trifluoromethanesulfonate (1.7 mL, 9.38 mmol). The reaction medium is stirred for 30 minutes at 0° C. and then for 30 minutes at room temperature. N-Diisopropylethylamine (1 mL) is added and the mixture is stirred for 15 minutes and then concentrated to dryness under reduced pressure. The residue is purified by chromatography on silica gel (3:2 cyclohexane/ethyl acetate) to give the expected compound (1.7 g, 69%) in the form of white crystals.

Melting point 185-188° C.

$^1$H NMR (400 MHz, $CDCl_3$): δ 7.97-7.28 (m, 15H, H-aro), 7.17 (m, 2H, H-aroPMB), 6.72 (m, 3H, H-aroPMB, H-1), 6.54 (d, 1H, J 8.5 Hz, H-2), 6.13 (t, 1H, J 10.0 Hz, H-4'), 5.90 (t, 1H, J 10.0 Hz, H-3'), 5.72 (m, 1H, H-8), 5.67 (m, 1H, H-2'), 5.61 (d, 2H, J 5.0 Hz, $CH_2PhOCH_3$), 5.43 (d, 1H, J 7.0 Hz, H-1'), 5.32 (d, 1H, J 10.0 Hz, H-5'), 5.25 (m, 1H, H-7), 5.00-4.80 (m, 2H, H-9, H-5), 4.40 (m, 1H, H-6), 4.20 (m, 2H, $OCH_2CH_3$), 4.00 (m, 1H, H-16a), 3.74 (s, 3H, $OCH_3$), 3.00 (m, 1H, H-16b), 2.84-2.74 (m, 2H, H-10), 2.48 (m, 1H, H-14), 1.89 (m, 2H, H-15), 1.30 (m, 12H, $C(CH_3)_3$, $OCH_2CH_3$).

$^{13}$C NMR (100 MHz, $CDCl_3$): δ 176.4, 165.7, 165.1, 164.5, 159.9 (C=O, C=N), 155.0, 150.5, 133.1, (C-aro), 130.7 (C-8), 129.8, 129.7, 129.6, 128.3, 128.2, 128.1, (C-aro), 127.4 (C-7), 122.2 (C-1), 119.3 (C-2), 114.3 (C-aroPMB), 99.4 (C-1'), 89.9 (C-5), 72.9 (C-3', C-6), 72.5 (C-2'), 71.5 (C-4'), 68.7 (C-5'), 61.6 ($OCH_2CH_3$), 56.6 ($CH_2PhOCH_3$), 55.2 ($OCH_3$), 50.2 (C-9), 44.3 (C-13), 39.8 (C-14), 37.2 (C-16), 35.3 (C-15), 35.0 ($C(CH_3)_3$), 30.2 (C-10), 29.8 ($C(CH_3)_3$), 14.7 ($OCH_2CH_3$).

Mass calculated for $C_{59}H_{57}N_5O_{14}Na$ $[M+Na]^+$ 1082.3800, found 1082.3802.

1.7. 3-O-pivaloyl-N-ethoxycarbonylnormorphin-6-yl 2,3,4-tri-O-benzoyl-5-C-(tetrazol-5-yl)-β-D-xylopyranoside A solution of the compound obtained in step 1.6 (1.6 g, 1.51 mmol) in trifluoroacetic acid (4.5 mL, 60.6 mmol) is refluxed for 15 minutes. The reaction medium is concentrated to dryness, and the residue is taken up in toluene (2×10 mL) and reconcentrated. The residue is purified by chromatography on silica gel (1:2 cyclohexane/ethyl acetate) to give the expected compound (850 mg, 60%) in the form of pale yellow crystals.

Melting point 169-171° C.

$^1$H NMR (400 MHz, $CDCl_3$): δ 7.98-7.24 (m, 15H, H-aro), 6.76 (d, 1H, J 8.0 Hz, H-1), 6.58 (d, 1H, J 8.0 Hz, H-2), 6.01 (t, 1H, J 10.0 Hz, H-3'), 5.98-5.95 (m, 1H, H-8), 5.72 (m, 1H, H-4'), 5.62 (m, 1H, H-2'), 5.41 (d, 1H, J 10.0 Hz, H-5'), 5.34-5.26 (m, 2H, H-1' and H-7), 5.02-4.96 (m, 1H, H-9), 4.85 (m, 1H, H-5), 4.38-4.31 (m, 1H, H-6), 4.22-4.13 (m, 2H, $OCH_2CH_3$), 4.07-3.98 (m, 1H, H-16a), 3.10-2.83 (m, 2H, H-16b, H-10a), 2.82-2.72 (m, 1H, H-10b), 2.47 (m, 1H, H-14), 1.93-1.85 (m, 2H, H-15), 1.47 (s, 9H, $C(CH_3)_3$), 1.33-1.25 (m, 3H, $OCH_2CH_3$).

$^{13}$C NMR (100 MHz, $CDCl_3$): δ 165.6, 165.1, 165.0 (C=O, C=N), 133.5, 132.4, 130.0, 129.8, 128.5, 128.4, 128.3 (C-aro, C-8, C-7), 122.5 (C-1), 119.9 (C-2), 90.9 (C-1'), 77.0 (C-6), 72.0 (C-2' or C-3'), 71.9 (C-2' or C-3'), 70.7 (C-4'), 68.3 (C-5'), 61.8 ($OCH_2CH_3$), 49.7 (C-9), 44.5 (C-13), 40.0 (C-14), 37.1 (C-16), 35.5 (C-15), 29.7 (C-10), 27.2 ($C(CH_3)_3$), 14.7 ($OCH_2CH_3$).

Mass calculated for $C_{51}H_{49}N_5O_{13}Na$ $[M+Na]^+$ 962.3225, found 962.3211.

1.8. Morphin-6-yl 5-C-(tetrazol-5-yl)-β-D-xylopyranoside trifluoroacetate (compound 2)

To a suspension of lithium aluminium hydride (300 mg, 7.91 mmol) in tetrahydrofuran (12 mL) is added a solution of the compound obtained in step 1.7 (500 mg, 0.532 mmol) in tetrahydrofuran (12 mL). The reaction medium is stirred for 1 hour at reflux. Ethyl acetate is added to destroy the excess lithium aluminium hydride and the medium is brought to pH 1 by adding 1N hydrochloric acid solution. The reaction medium is concentrated to dryness. The residue is purified a first time on a reverse-phase chromatography column (pure $H_2O$ and then 80:20 ($H_2O$+0.1% trifluoroacetic acid)/acetonitrile) to remove the salts. A second purification by reverse-phase preparative chromatography (95:5 to 20:80 gradient of ($H_2O$+0.1% trifluoroacetic acid)/acetonitrile) gives the expected compound in the form of white crystals (42 mg, 16%).

Melting point 204-207° C.

¹H NMR (400 MHz, D₂O): δ 6.74 (d, 1H, J 8.0 Hz, H-1), 6.65 (d, 1H, J 8.0 Hz, H-2), 5.73 (m, 1H, H-8), 5.30 (m, 1H, H-7), 5.23 (d, 1H, J 5.5 Hz, H-5), 4.94-4.88 (m, 2H, H-1', H-5'), 4.48 (m, 1H, H-6), 4.15 (m, 1H, H-9), 3.80 (t, 1H, J 9.5 Hz, H-4'), 3.69 (t, 1H, J 9.5 Hz, H-3'), 3.54 (m, 1H, H-2'), 3.37 (m, 1H, H-16), 3.24 (m, 1H, H-10a), 3.10 (m, 1H, H-16b), 2.95 (s, 3H, NCH₃), 2.95-2.83 (m, 2H, H-10b, H-14), 2.32-2.02 (m, 2H, H-15).

¹³C NMR (100 MHz, D₂O): δ 145.5 (C=N), 137.8, 134.0 (C-ipso), 131.1 (C-8), 129.0 (C-ipso), 126.0 (C-7), 123.3 (C-ipso), 120.4 (C-2), 117.7 (C-1), 102.3 (C-1'), 88.1 (C-5), 75.0 (C-3'), 73.3 (C-6), 73.0 (C-2'), 72.4 (C-4'), 69.3 (C-5'), 60.5 (C-9), 47.1 (C-16), 41.5 (C-13), 40.9 (NCH₃), 38.4 (C-14), 32.4 (C-15), 20.8 (C-10).

Mass calculated for $C_{23}H_{28}N_5O_7$ [M+H]⁺ 486.1989, found 486.1982.

Example 2

Morphin-6-yl 5-C-(2-methyl-1,3,4-oxadiazol-5-yl)-β-D-xylopyranoside trifluoroacetate (compound 5)

2.1. 3-O-acetylmorphin-6-yl 2,3,4-tri-O-acetyl-5-C-(2-methyl-1,3,4-oxadiazol-5-yl)-β-D-xylopyranoside A solution of morphin-6-yl 5-C-(tetrazol-5-yl)-β-D-xylopyranoside trifluoroacetate (134 mg, 0.28 mmol), obtained in step 1.8 of Example 1, in acetic anhydride (3 mL) is refluxed overnight. The reaction medium is concentrated to dryness and the residue is taken up in toluene (2×10 mL) and reconcentrated. The product is purified by chromatography on silica gel (98:2 to 95:5 chloroform/methanol) to give the expected compound (102 mg, 55%) in the form of pale yellow crystals.

Melting point 180-186° C.

¹H NMR (400 MHz, CDCl₃): δ 6.77 (d, 1H, J 8.0 Hz, H-1), 6.59 (d, 1H, J 8.0 Hz, H-2), 5.71 (m, 1H, H-8), 5.37 (m, 2H, H-4' and H-3'), 5.27 (m, 1H, H-7), 5.18 (m, 1H, H-2'), 4.99 (d, 1H, J 7.5 Hz, H-1'), 4.95 (d, 1H, J 5.5 Hz, H-5), 4.87 (m, 1H, H-5'), 4.31 (m, 1H, H-6), 3.71 (m, 1H, H-9), 3.07 (m, 1H, H-10a), 2.97-2.89 (m, 2H, H-16a, H-14), 2.62-2.52 (m, 8H, H-10b, CH₃oxadiazole, NCH₃, H-16b), 2.33 (s, CH₃CO), 2.28 (m, 1H, H-15a), 2.14 (s, 3H, CH₃CO), 2.04 (s, 3H, CH₃CO), 1.98 (m, 1H, H-15b), 1.93 (s, 3H, CH₃CO).

¹³C NMR (100 MHz, CDCl₃): δ 175.9, 170.0, 169.4, 169.3, 165.3, 161.2 (C=O, C=N), 150.3, 132.0 (C-ipso), 130.9 (C-8), 130.6, 130.4 (C-ipso), 127.5 (C-7), 122.6 (C-1), 119.5 (C-2), 100.0 (C-1'), 89.1 (C-5), 73.6 (C-6), 71.8 (C-3' or C-4'), 71.0 (C-2'), 69.6 (C-3' or C-4'), 67.9 (C-5'), 58.5 (C-9), 46.0 (C-16), 42.7 (C-13), 41.7 (NCH₃), 38.9 (C-14), 33.8 (C-15), 21.5 (C-10), 20.7, 20.6, 20.4 (CH₃CO), 11.0 (CH₃oxadiazole).

Mass calculated for $C_{33}H_{38}N_3O_{12}$ [M+H]⁺ 668.2455, found 668.2560.

2.2. Morphin-6-yl 5-C-(2-methyl-1,3,4-oxadiazol-5-yl)₄₃-D-xylopyranoside trifluoroacetate (Compound 5)

To a solution of 3-O-acetylmorphin-6-yl 2,3,4-tri-O-acetyl-5-C-(2-methyl-1,3,4-oxadiazol-5-yl)-β-D-xylopyranoside prepared beforehand (100 mg, 0.15 mmol) in methanol (2 mL) at room temperature is added sodium methoxide (32 mg, 0.59 mmol). The reaction medium is stirred for 3 hours at room temperature and then neutralized by addition of resin sold under the name Amberlyte H⁺® (Rohm & Haas). The solution is filtered and the filtrate concentrated under reduced pressure. The residue is purified by reverse-phase preparative chromatography (95:5 to 20:80 gradient of (H₂O+0.1% trifluoroacetic acid)/acetonitrile) to give the expected product (34 mg, 46%) in the form of white crystals.

Melting point 215-218° C.

¹H NMR (300 MHz, D₂O): δ 6.83 (d, 1H, J 8.0 Hz, H-1), 6.74 (d, 1H, J 8.0 Hz, H-2), 5.84 (m, 1H, H-8), 5.46 (m, 1H, H-7), 5.32 (d, 1H, J 6.5 Hz, H-5), 5.00 (d, 1H, J 8.0 Hz, H-1'), 4.90 (m, 1H, H-5'), 4.59 (m, 1H, H-6), 4.26 (m, 1H, H-9), 3.92 (t, 1H, J 9.5 Hz, H-4'), 3.74 (t, 1H, J 9.5 Hz, H-3'), 3.59 (m, 1H, H-2'), 3.45-3.38 (m, 1H, H-16a), 3.29 (d, 1H, H-10a), 3.17 (m, 1H, H-16b), 3.03-2.92 (m, 5H, NCH₃, H-10b, H-14), 2.63 (s, 3H, CH₃oxadiazole), 2.40-2.11 (m, 2H, H-15).

¹³C NMR (75 MHz, D₂O): δ 131.2 (C-8), 126.3 (C-7), 120.6 (C-2), 118.2 (C-1), 102.5 (C-1'), 88.2 (C-5), 75.0 (C-3'), 73.5 (C-6), 73.0 (C-2' or C-4'), 71.4 (C-2' or C-4'), 69.3 (C-5'), 60.7 (C-9), 47.4 (C-6), 41.1 (NCH₃), 38.7 (C-14), 32.6 (C-15), 21.1 (C-10), 10.2 (CH₃oxadiazole).

Mass calculated for $C_{25}H_{30}N_3O_8$ [M+H]⁺ 500.2033, found 500.2021.

Example 3

Morphin-6-yl 5-C-[5-(4-methoxyphenyl)-4-(2,2,2-trifluoroethyl)-4H-1,2,4-triazol-3-yl]-β-D-xylopyranoside trifluoroacetate (compound 6)

3.1. 1,2,3,4-tetra-O-benzoyl-5-C-[5-(4-methoxyphenyl)-4-(2,2,2-trifluoro-ethyl)-4H-1,2,4-triazol-3-yl]-α/β-D-xylopyranose To a solution of 1,2,3,4-tetra-O-benzoyl-5-C-(tetrazol-5-yl)-α/β-D-xylopyranose (10.0 g, 15.77 mmol), obtained in step 1.2 of Example 1, in toluene (119 mL) are added triethylamine (4.3 mL, 30.85 mmol) and 2,2,2-trifluoro-N-(4-methoxybenzyl)acetimidoyl chloride (7.9 g, 31.47 mmol). The reaction medium is stirred overnight at reflux. The solvent is removed under reduced pressure and the residue purified by chromatography on silica gel (1:1 cyclohexane/ethyl acetate) to give the expected product (7.3 g, 56%) in the form of pale yellow crystals. The proton NMR spectrum in CDCl₃ shows a ratio α:β of 5:2.

¹H NMR (400 MHz, CDCl₃): δ 8.28-7.29 (m, 22Hα+22Hβ, H-aro), 7.00 (d, 2Hα, J 8.5 Hz, H-aroPMPα), 6.94 (d, 2Hβ, J 8.5 Hz, H-aroPMPβ, 6.84 (d, 1Hα, J 3.5 Hz, H-1α), 6.54 (t, 1Hβ, J 8.5 Hz, H-4β), 6.45 (m, 2Hα, H-3α, H-4α), 6.38 (d, 1Hβ, J 7.0 Hz, H-1β), 6.18 (t, 1Hβ, J 8.5 Hz, H-3β), 5.94 (dd, 1Hβ, J 7.0 Hz, J 8.5 Hz, H-2β), 5.76-5.69 (m, 2Hα, H-2α, H-5α), 5.61 (d, 1Hβ, J 8.5 Hz, H-5β, 5.13 (m, 1H β CH₂CF₃β, 4.99 (m, 1Hα CH₂CF₃α), 4.65-4.51 (m, 1Hα+1Hβ CH₂CF₃α, CH₂CF₃β ), 3.84 (s, 3Hα, OCH₃α), 3.83 (s, 3Hβ, OCH₃β).

¹³C NMR: (100 MHz, CDCl₃) δ 166.0, 165.4, 165.2, 164.7 (C=O), 161.5, 156.8, 149.5 (C=N, C-ipsoPMP), 134.4-128.2 (C-aro), 117.5 (C-ipsoPMP), 114.6 (C-aroPMPα), 114.5 (C-aroPMPβ), 93.2 (C-1β), 90.1 (C-1α), 71.9 (C-2β or C-3β or C-4β), 70.3 (C-2α or C-2α or C-4α), 70.2 (C-2α or C-2α or C-4α), 70.0 (C-2β or C-3β or C-4β), 69.2 (C-2α or C-2α or C-4α), 69.1 (C-2β or C-3β or C-4β), 66.1 (C-5α, C-5β), 55.4 (OCH₃α, OCH₃β), 45.4 (CH₂CF₃β), 45.0 (CH₂CF₃α).

Mass calculated for $C_{44}H_{35}F_3N_3O_{10}$ [M+H]⁺ 822.2275, found 822.2291.

3.2. 2,3,4-tri-O-benzoyl-5-C-[5-(4-methoxyphenyl)-4-(2,2,2-trifluoroethyl)-4H-1,2,4-triazol-3-yl]α/β-D-xylopyranose To a solution of the compound prepared in step 3.1 (7.2 g, 8.77 mmol) in N,N-dimethylformamide (50 mL), at 0° C., is added hydrazine acetate (1.2 g, 13.0 mmol) portionwise over 15 minutes. The reaction medium is stirred for 1 hour at 0° C. and then for 2.5 hours at room temperature. Ethyl acetate (100 mL) and water (50 mL) are added. The phases are separated. The aqueous phase is re-extracted with ethyl acetate (1×50 mL). The combined organic phases are dried over sodium sulfate. The solvent is removed under reduced pressure and the residue purified by chromatography on silica gel (2:3 cyclohexane/ethyl acetate) to give the expected product (3.1 g, 49%) in the form of white crystals. The proton NMR spectrum in $CDCl_3$ shows a ratio α/β of 9:1.

$^1H$ NMR (400 MHz, $CDCl_3$) for the α anomer 7.99-7.26 (m, 17H, H-aro), 6.76 (d, 2H, J 9.0 Hz, H-aroPMP), 6.24 (t, 1H, J 10.0 Hz, H-3), 6.14 (t, 1H, J 10.0 Hz, H-4), 5.80 (d, 1H, J 10.0 Hz, H-5), 5.45 (d, 1H, J 3.0 Hz, H-1), 5.31 (m, 1H, $CH_2CF_3$), 5.07 (dd, 1H, J 3.0 Hz, J 10.0 Hz, H-2), 4.92 (m, 1H, $CH_2CF_3$), 3.72 (s, 3H, $OCH_3$).

$^{13}C$ NMR (100 MHz, $CDCl_3$) for the α anomer: δ 165.8, 165.5, 165.1 (C=O) 161.3, 156.5, 151.3 (C=N, C-ipsoPMP), 133.2-128.2 (C-aro), 122.9 (C-ipso) 117.6 (C-ipsoPMP), 114.4 (C-aroPMP), 90.2 (C-1), 72.1 (C-2), 70.8 (C-3), 69.6 (C-4), 62.1 (C-5), 55.2 ($OCH_3$), 45.3 (m, $CH_2CF_3$).

Mass calculated for $C_{37}H_{31}F_3N_3O_9$ $[M+H]^+$ 718.2012, found 718.2034.

3.3. 2,3,4-tri-O-benzoyl-5-C-[5-(4-methoxyphenyl)-4-(2,2,2-trifluoroethyl)-4H-1,2,4-triazol-3-yl]α/β-D-xylopyranosyl trichloroacetimidate To a solution of the product prepared in step 3.2 (2.8 g, 3.91 mmol) in dichloromethane (65 mL) at room temperature are added 1,8-diazabicyclo[5.4.0]undec-7-ene (115 µL, 0.770 mmol) and then trichloroacetonitrile (7.8 ml, 77.8 mmol). The reaction medium is stirred for 1 hour at room temperature. A solution of acetic acid (45 µL, 0.786 mmol) in water (25 mL) is added. The phases are separated, the organic phase is washed with water (25 mL) and then dried over sodium sulfate. The solvent is removed under reduced pressure and the residue purified by chromatography on silica gel (silica neutralized beforehand by washing with a 5% solution of triethylamine in ethyl acetate) (7:3 cyclohexane/ethyl acetate) to give the expected product (2.1 g, 63%) in the form of white crystals. The proton NMR spectrum in $CDCl_3$ shows a ratio α/β of 5:4.

$^1H$ NMR (400 MHz, $CDCl_3$): δ 8.78 (s, 1Hβ, NHβ), 8.77 (s, 1Hα, NHα), 8.00-7.31 (m, 17Hα+17Hβ, H-aro), 7.00 (m, 2Hα+2Hβ, H-aroPMPα, H-aroPMPβ), 6.78 (d, 1Hα, J 3.5 Hz, H-1α), 6.51 (t, 1Hα, J 10.0 Hz, H-4α), 6.44-6.34 (m, 1Hα+1Hβ, H-3α, H-4β), 6.21 (d, 1Hβ, J 8.0 Hz, H-1β), 6.13 (t, 1Hβ, J 9.5 Hz, H-3β), 5.92 (dd, 1Hβ, J 8.0 Hz, J 9.5 Hz, H-2β), 5.69 (d, 1Hα, J 10.0 Hz, H-5α), 5.62 (dd, 1Hα, J 3.5 Hz, J 10.0 Hz, H-2α), 5.52 (d, 1Hβ, J 9.5 Hz, H-5β), 5.27 (m, 1Hβ, $CH_2CF_3$β), 5.00 (m, 1Hα, $CH_2CF_3$α), 4.58 (m, 1Hα+1Hβ, $CH_2CF_3$α, $CH_2CF_3$β), 3.87 (s, 3Hα+3Hβ, $OCH_3$α, $OCH_3$β).

$^{13}C$ NMR (100 MHz, $CDCl_3$) δ 165.7, 165.4, 164.7, 164.4, (O=O) 161.4, 149.2 (C=N, C-ipsoPMP), 133.7-128.2 (C-aro), 117.7 (C-ipsoPMP), 114.5 (C-aroPMP), 96.6 (C-1β), 93.5 (C-1α), 72.5, 70.5, 70.2, 70.0, 69.3, 68.9 (C-2α, C-3β, C-3α, C-3β C-4α, C-4β), 66.2 (C-5α, C-5β), 55.4 ($OCH_3$α, $OCH_3$β), 45.1 (m, $CH_2CF_3$α, $CH_2CF_3$β).

3.4. 3-O-pivaloyl-N-ethoxycarbonylnormorphin-6-yl 2,3,4-tri-O-benzoyl-5-C-[5-(4-methoxyphenyl)-4-(2,2,2-trifluoroethyl)-4H-1,2,4-triazol-3-yl]-β-D-xylopyranoside To a solution of the product prepared in step 3.3 (1.20 g, 1.40 mmol) and 3-O-pivaloyl-N-ethoxycarbonylnormorphine (410 mg, 0.96 mmol) in dichloromethane (50 mL) at 0° C. under argon is added trimethylsilyl trifluoromethanesulfonate (696 µL, 3.84 mmol). The reaction medium is stirred for 30 minutes at 0° C. and then for 30 minutes at room temperature. N-Diisopropylethylamine (0.5 mL) is added and the mixture is stirred for 15 minutes and then concentrated to dryness under reduced pressure. The residue is purified by chromatography on silica gel (3:7 cyclohexane/ethyl acetate) to give the expected compound (680 mg, 63%) in the form of orange crystals.

Melting point 194° C.

$^1H$ NMR (400 MHz, $CDCl_3$) δ 7.98-7.29 (m, 17H, H-aro), 7.03 (d, 2H, J 9.0 Hz, H-aroPMP), 6.71 (d, 1H, J 8.0 Hz, H-1), 6.54 (d, 1H, J 8.0 Hz, H-2), 6.00 (m, 2H, H-3', H-4'), 5.73 (m, 1H, H-8), 5.66 (m, 1H, H-2'), 5.41 (m, 2H, H-1', H-5'), 5.30 (m, 1H, H-7), 4.98 (m, 2H, H-9, $CH_2CF_3$), 4.86-4.76 (m, 2H, H-5, $CH_2CF_3$), 4.30 (m, 1H, H-6), 4.17 (m, 2H, $OCH_2CH_3$), 4.01 (m, 1H, H-16a), 3.89 (s, 3H, $OCH_3$), 3.07-2.84 (m, 2H, H-16b, H-10a), 2.75 (m, 1H, H-10b), 2.47 (m, 1H, H-14), 1.88 (m, 2H, H-15), 1.27 (m, 12H, $C(CH_3)_3$, $OCH_2CH_3$).

$^{13}C$ NMR (100 MHz, $CDCl_3$) δ 165.6, 165.1, 165.0, (C=O) 161.4, 156.9, 149.6 (C=N, C-ipsoPMP), 133.4 (C-aro), 130.7 (C-8), 129.9-127.8 (C-aro, C-7), 122.5 (C-1), 118.0 (C-ipsoPMP), 119.4 (C-2), 114.6 (C-aroPMP), 100.6 (C-1'), 90.2 (C-5), 74.0 (C-6), 72.3 (C-2' or C-3' or C-4'), 71.8 (C-2' or C-3' or C-4'), 70.3 (C-2', C-3' or C-4'), 69.9 (C-5'), 61.7 ($OCH_2CH_3$), 55.4 ($OCH_3$), 48.1 (C-9), 44.5 ($CH_2CF_3$ or C-13), 39.8 (C-14), 37.2 (C-16), 35.3 (C-15), 35.0 ($C(CH_3)_3$), 30.0 (C-10), 27.1 ($C(CH_3)_3$), 14.7 ($OCH_2CH_3$).

Mass calculated for $C_{61}H_{58}F_3N_4O_{14}$ $[M+H]^+$ 1127.3902, found 1127.3889.

3.5. Morphin-6-yl 5-C-[5-(4-methoxyphenyl)-4-(2,2,2-trifluoroethyl)-4H-1,2,4-triazol-3-yl]-β-D-xylopyranoside trifluoroacetate (Compound 6)

To a suspension of lithium aluminium hydride (311 mg, 8.19 mmol) in tetrahydrofuran (13 mL) is added a solution of the compound obtained in step 3.4 (622 mg, 0.55 mmol) in tetrahydrofuran (13 mL). The reaction medium is stirred for 1 hour at reflux. Ethyl acetate is added to destroy the excess $LiAlH_4$ and the medium is brought to pH 1 by adding 1N hydrochloric acid solution. The reaction medium is concentrated to dryness. The residue is purified by passing twice successively through a reverse-phase chromatography column (pure $H_2O$ then 80:20 ($H_2O$+0.1% trifluoroacetic acid)/$CH_3CN$) to remove the salts. A final purification by preparative reverse-phase chromatography (95:5 to 20:80 gradient ($H_2O$+0.1% trifluoroacetic acid)/acetonitrile) gives the expected compound in the form of white crystals (35 mg, 10%).

Melting point 274-276° C.

$^1H$ NMR (400 MHz, $D_2O$): δ 7.51 (d, 2H, J 8.5 Hz, H-aroPMP), 7.15 (d, 2H, J 8.5 Hz, H-aroPMP), 6.72 (d, 1H, J 8.0 Hz, H-1), 6.64 (d, 1H, J 8.0 Hz, H-2), 5.67 (m, 1H, H-8), 5.29 (m, 1H, H-7), 5.22 (d, 1H, J 6.0 Hz, H-5), 5.09-4.90 (m, 3H, $CH_2CF_3$, H-1'), 4.82 (d, 1H, J 9.5 Hz, H-5'), 4.41 (m, 1H, H-6), 4.18 (m, 1H, H-9), 4.12 (t, 1H, J 9.5 Hz, H-4'), 3.88 (s, 3H, $OCH_3$), 3.71 (t, 1H, J 9.5 Hz, H-3'), 3.57 (dd, 1H, J 8.0 Hz, J 9.5 Hz, H-2'), 3.36 (m, 1H, H-16a) 3.26 (m, 1H, H-10a), 3.12-3.03 (m, 1H, H-16b), 2.96 (s, 3H, N—$CH_3$), 2.93-2.84 (m, 2H, H-10b, H-14), 2.31-2.22 (m, 2H, H-15).

$^{13}C$ NMR (100 MHz, $D_2O$): δ 130.9 (C-aroPMP), 126.0 (C-7), 120.4 (C-2), 117.7 (C-1), 116.8 (C-ipsoPMP), 114.7 (C-aroPMP), 102.6 (C-1'), 88.1 (C-5), 75.0 (C-3'), 73.6 (C-6), 72.8 (C-2'), 72.0 (C-4'), 67.9 (C-5'), 60.5 (C-9), 55.4 ($OCH_3$), 47.2 (C-16), 46.6 ($CH_2CF_3$), 40.9 ($NCH_3$), 38.4 (C-14), 32.4 (C-15), 20.8 (C-10).

Mass calculated for $C_{33}H_{36}F_3N_4O_8$ [M+H]$^+$ 673.2485, found 673.2482.

Example 4

Morphin-6-yl 5-C-(tetrazol-5-yl)-αβ-D-xylopyranoside trifluoroacetate (compound 1)

4.1 3-O-pivaloyl-N-ethoxycarbonylnormorphin-6-yl-2,3,4-tri-O-benzoyl-5-C-(tetrazol-5-yl)-α/β-D-xylopyranoside A solution of 3-O-pivaloyl-N-ethoxycarbonylnormorphin-6-yl 2,3,4-tri-O-benzoyl-5-C-[2-(4-methoxybenzyl)-2H-tetrazol-5-yl]-β-D-xylopyranoside (1.6 g, 1.51 mmol), obtained in step 1.6 of Example 1, in trifluoroacetic acid (4.5 mL, 60.6 mmol) is refluxed for 45 minutes. The reaction medium is concentrated to dryness and the residue is taken up in toluene (2×10 mL) and concentrated again. Filtration on silica gel (ethyl acetate) allows the apolar impurities to be removed. The residue (1.3 g) is used in the reduction step without further purification.

4.2 Morphin-6-yl 5-C-(tetrazol-5-yl)-αβ-D-xylopyranoside trifluoroacetate (compound 1)

Morphin-6-yl 5-C-(tetrazol-5-yl)α/β-D-xylopyranoside trifluoroacetate is synthesized from 3-O-pivaloyl-N-ethoxycarbonylnormorphin-6-yl2,3,4-tri-O-benzoyl-5-C-(tetrazol-5-yl)-α/β-D-xylopyranoside obtained previously (1.30 g, 1.38 mmol) according to the same procedure as that described in step 1.8 of Example 1.

The expected mixture of anomers is obtained in the form of pale yellow crystals (215 mg, 32%). The proton NMR spectrum in D$_2$O shows a ratio α:β of 1:1.

$^1$H NMR (400 MHz, D$_2$O): δ 6.83-6.79 (m, 1Hα+1Hβ, H-1α, H-1β), 6.70 (m, 1Hα+1Hβ, H-2α, H-2β ), 5.91 (m, 1H α, H-8α), 5.82 (m, 1Hβ, H-8β, 5.60 (d, 1Hα, J 10.0 Hz, H-5'α), 5.48 (m, 1Hα, H-7α ), 5.39 (m, 1Hβ, H-7β), 5.31 (d, 1Hα, J 4.0 Hz, H-1'α), 5.28 (d, 1Hβ, J 6.0 Hz, H-5β, 5.13 (d, 1Hα, J 6.0 Hz, H-5α), 5.01-4.96 (m, 2Hβ, H-5'β, H-1'β, 4.55 (m, 1Hβ, H-6β, 4.43 (m, 1Hα H-6α), 4.26-4.17 (m, 1Hα+1Hβ, H-9α, H-9β, 3.99 (t, 1Hα, J 9.5 Hz, H-3'α), 3.82 (dd, 1Hα, J 4.0 Hz, J 9.5 Hz, H-2'α), 3.78-3.74 (m, 1Hα+2Hβ, H-4'α, H-3'α, H-4'β), 3.59 (m, 1Hβ, H-2'β), 3.41-3.38 (m, 1Hα+1Hβ, H-16aα, H-16aβ), 3.33-3.27 (m, 1Hα+1Hβ, H-10aα, H-10aβ), 3.17-3.08 (m, 1Hα+1Hβ, H-16bα, H-16bβ), 3.00 (s, 3Hα+3Hβ, NCH$_3$α, NCH$_3$β), 3.00-2.88 (m, 2Hα+2Hβ, H-10bα, H-10bβ, H-14α, H-14β), 2.37-2.07 (m, 2Hα+2Hβ, H-15α, H-15β).

$^{13}$C NMR (100 MHz, D$_2$O): δ 136.5 (C-ipso), 131.2 (C-8α), 130.4 (C-8β), 129.0 (C-ipso), 126.5 (C-7α), 126.1 (C-7β), 123.3 (C-ipso), 120.5 (C-2α, C-2β), 117.8 (C-1α, C-1β), 102.5 (C-1'β), 100.0 (C-1'α), 90.1 (C-5α), 88.2 (C-5β), 74.9, 74.7, 73.6, 72.9, 72.5, 72.4, 72.3, 71.1 (C-2'α, C-2'β, C-3'α, C-3'β, C-4'α, C-4'β, C-6α, C-6β), 68.9 (C-5'β), 65.6 (C-5'α), 60.5 (C-9α, C-9β), 47.2 (C-16α, C-16β), 41.5 (C-13α, C-13β), 40.9 (NCH$_3$α, NCH$_3$β), 38.7 (C-14α), 38.4 (C-14β), 32.4 (C-15α, C-15β), 20.9 (C-10α, C-10β).

Mass calculated for $C_{23}H_{28}N_5O_7$ [M+H]$^+$486.1989, found 486.1979.

Example 5

Morphin-6-yl 5-C-(2-methyl-1,3,4-oxadiazol-5-yl)-α-D-xylopyranoside trifluoroacetate (compound 4)

5.1 3-O-acetylmorphin-6-yl 2,3,4-tri-O-acetyl-5-C-(2-methyl-1,3,4-oxadiazol-5-yl)-α-D-xylopyranoside trifluoroacetate and 3-O-acetylmorphin-6-yl 2,3,4-tri-O-acetyl-5-C-(2-methyl-1,3,4-oxadiazol-5-yl)-α/β-xylopyranoside trifluoroacetate A solution of morphin-6-yl 5-C-(tetrazol-5-yl)α/β-D-xylopyranoside trifluoroacetate (300 mg, 0.62 mmol), obtained in step 4.2 of Example 4, in acetic anhydride (7 mL) is refluxed overnight. The reaction medium is concentrated to dryness and the residue is taken up in toluene (2×10 mL) and concentrated again. The product is purified on a column of silica (from 98:2 to 95:5 CHCl$_3$—CH$_3$OH) to give two fractions:
one containing the pure α anomer (45 mg)
the other containing a mixture of the α and β anomers (92 mg). The proton NMR spectrum in CDCl$_3$ shows a ratio α/β of 2:3 estimated by NMR and by HPLC. The overall reaction yield is 33%.

$^1$H NMR (400 MHz, CDCl$_3$) for the α anomer: δ 6.82 (d, 1H, J 8.0 Hz, H-1), 6.61 (d, 1H, J 8.0 Hz, H-2), 5.74 (m, 1H, H-8), 5.69 (t, 1H, J 10.0 Hz, H-3'), 5.63 (d, 1H, J 10.0 Hz, H-5'), 5.40 (d, 1H, J 4.0 Hz, H-1'), 5.37-5.30 (m, 2H, H-4', H-7), 5.01-4.96 (m, 2H, H-2', H-5), 4.14 (m, 1H, H-6), 3.60 (m, 1H, H-9), 3.10 (m, 1H, H-10a), 2.80 (m, 1H, H-16a), 2.70-2.50 (m, 9H, CH$_3$oxadiazole, NCH$_3$, H-10b, H-14, H-16b), 2.34 (s, 3H, CH$_3$CO), 2.31-2.25 (m, 1H, H-15a), 2.08 (s, 3H, CH$_3$CO), 2.05 (s, 3H, CH$_3$CO), 2.00 (m, 1H, H-15b), 1.95 (s, 3H, CH$_3$CO).

$^{13}$C NMR (100 MHz, CDCl$_3$) for the α anomer: δ 170.2, 169.2, 168.6, 164.9, 162.2 (C=O, C=N), 122.7 (C-1), 119.4 (C-2), 97.6 (C-1'), 91.4 (C-5), 76.7 (C-6), 70.6 (C-2'), 70.0 (C-4'), 69.2 (C-3'), 64.2 (C-5'), 59.2 (C-9), 46.4 (C-16), 42.5 (NCH$_3$), 33.5 (C-15), 21.3 (C-10), 20.7, 20.6, 20.5 (CH$_3$CO), 11.0 (CH$_3$-oxadiazole).

Mass calculated for $C_{33}H_{38}N_3O_{12}$ [M+H]$^+$ 668.2455, found 668.2560.

5.2 morphin-6-yl 5-C-(2-methyl-1,3,4-oxadiazol-5-yl)-α-D-xylopyranoside trifluoroacetate (compound 4)

To a solution of 3-O-acetylmorphin-6-yl 2,3,4-tri-O-acetyl-5-C-(2-methyl-1,3,4-oxadiazol-5-yl)-α-D-xylopyranoside trifluoroacetate (45 mg, 0.07 mmol) in methanol (0.5 mL), at room temperature is added sodium methoxide (14 mg, 0.26 mmol). The reaction medium is stirred for 3 hours at room temperature and then neutralized by adding Amberlyte H$^+$® resin (Rohm & Haas). The solution is filtered and the filtrate concentrated under reduced pressure to give morphin-6-yl 5-C-(2-methyl-1,3,4-oxadiazol-5-yl)-α-D-xylopyranoside trifluoroacetate (31 mg, 92%) in the form of pale yellow crystals.

$^1$H NMR (400 MHz, CD$_3$OD) for the α anomer: δ 8.54 (s, 1H, PhOH), 6.57 (d, 1H, J 8.0 Hz, H-1), 6.46 (d, 1H, J 8.0 Hz, H-2), 5.86 (m, 1H, H-8), 5.49 (d, 1H, J 10.0 Hz, H-5'), 5.39 (m, 1H, H-7), 5.13 (d, 1H, J 4.0 Hz, H-1'), 4.95 (d, 1H, J 6.0 Hz, H-5), 4.24 (m, 1H, H-6), 3.84 (t, 1H, J 9.5 Hz, H-3'), 3.75 (dd, 1H, J 9.5 Hz, J 10.0 Hz, H-4'), 3.60-3.55 (m, 2H, H-9, H-2'), 3.08 (m, 1H, H-10a), 2.76-2.70 (m, 2H, H-14, H-16a), 2.59 (s, 3H, NCH$_3$), 2.56 (s, 3H, CH$_3$oxadiazole), 2.55-2.45 (m, 2H, H-10b, H-16b), 2.12 (m, 1H, H-15a), 1.84 (m, 1H, H-15b).

$^{13}$C NMR (100 MHz, CD$_3$OD) for the α anomer: 166.4, 166.3 (C=N), 147.6, 140.0 (C-ipso), 131.6 (C-8), 130.9

(C-ipso), 129.1 (C-7), 125.5 (C-ipso), 120.6 (C-2), 118.2 (C-1), 102.1 (C-1'), 92.1 (C-5), 78.0 (C-6), 74.7 (C-3'), 73.4 (C-2'), 73.3 (C-4'), 67.6 (C-5'), 60.9 (C-9), 47.7 (C-13), 44.6 (C-16), 42.5 (NCH$_3$), 40.7 (C-14), 35.4 (C-10), 22.3 (C-15), 10.8 (CH$_3$oxadiazole).

Mass calculated for $C_{25}H_{30}N_3O_8$ [M+H]$^+$ 500.2033, found: 500.2029 (a).

Example 6

Morphin-6-yl 5-C-(2-methyl-1,3,4-oxadiazol-5-yl)-α/β-D-xylopyranoside trifluoroacetate (compound 3)

The same protocol as that described in step 5.2 of Example 5 is used starting with the 3-O-acetylmorphin-6-yl 2,3,4-tri-O-acetyl-5-C-(2-methyl-1,3,4-oxadiazol-5-yl)-α/β-D-xylopyranoside (2:3 α:β) mixture (92 mg, 0.14 mmol) obtained in step 5.1 of Example 5. The expected mixture of anomers is obtained in the form of pale yellow crystals (62 mg, 90%). The proton NMR spectrum in CDCl$_3$ shows a ratio α/6 of 2:3 estimated by NMR and by HPLC.

Mass calculated for $C_{25}H_{30}N_3O_8$ [M+H]$^+$500.2033, found: 500.2585 (α:β 2:3).

The table that follows illustrates the chemical structures and the physical properties of a few examples of compounds according to the invention. In this table:

- in the "anomer" column, "α" and "β" represent, respectively, the pure α and β anomers and "α/β" represents a mixture thereof, the ratio in parentheses being the ratio (α:β);
- the "mass" column gives the result of the mass of the compound obtained according to the chemical ionization method;
- the "melting point" column indicates the melting point value of the compound in degrees Celsius;
- the "$α_D$" column indicates the optical rotation of the compound in degrees; the solvent and the measuring concentration are given in parentheses; and
- in the "salt" column, "CF$_3$COO$^-$" represents a compound in trifluoroacetate form.

animal's tail caused by a painful heat stimulus (infrared source). The "tail-flick" test (D'Amour-Smith test, 1941, Pharmacol. Exp. Ther.; 72: 74-79) consists, after administering a product, in placing a mouse's tail at the focal point of the infrared source so as to produce a nociceptive heat stimulus (surface temperature of about 55-60° C.). The mouse's reaction time (RT) (latency between the moment when the light beam is switched on and the moment when the mouse removes its tail) was measured in duplicate at different times ranging from 20 minutes to 120 minutes after administration of the product. The heat intensity is regulated such that this removal reflex is between 0.5 and 3.5 seconds in the control animals, and arbitrarily represents the criterion for minimum analgesia (0%). Two reaction time measurements were taken before administration of the product for each mouse, to establish a baseline measurement time. A maximum time of 8 seconds was chosen as the maximum reaction time so as not to induce tissue damage by burning the animals, and arbitrarily represents the criterion for maximum analgesia (100%). The reaction time is increased by the analgesics relative to a control animal not receiving any treatment. The products were administered subcutaneously and orally at doses of between 1.25 and 30 mg/kg (expressed as salt).

Results

The results obtained for the compounds of the invention are given in Table 2, which presents the following data:

- the maximum percentage of analgesic activity (% MPE max index) obtained for each compound (at a test dose),
- the ED$_{50}$ (expressed in mg/kg) corresponding to the effective dose for each compound for which 50% analgesia was obtained; this is calculated at a given time after administration of the compounds; and
- the duration of the analgesic action at a given dose.

The percentage of analgesic activity (% MPE) is determined by the following formula:

% MPE=(RTpost-administration−RTpre-administration)*100/(RTmax−RTpre-administration)

TABLE 1

| No. | R1 | Anomer | Mass | Melting point m.p. (° C.) | $α_D$ | Salt |
|---|---|---|---|---|---|---|
| 1 | tetrazole | α/β (1/1) | 486.1979 | — | — | CF$_3$COOH |
| 2 | tetrazole | β | 486.1982 | 204-207 | −116 (c = 0.5, CH$_3$OH) | CF$_3$COOH |
| 3 | 2-methyl-1,3,4-oxadiazole | α/β (2/3) | 500.2585 | — | — | CF$_3$COOH |
| 4 | 2-methyl-1,3,4-oxadiazole | α | 500.2029 | — | — | CF$_3$COOH |
| 5 | 2-methyl-1,3,4-oxadiazole | β | 500.2021 | 215-218 | — | CF$_3$COOH |
| 6 | 5(4-methoxy-phenyl)-4-(2,2,2-trifluoroethyl)-1,2,4-triazole | β | 673.2482 | 274-276 | −72 (c = 0.5, CH$_3$OH) | CF$_3$COOH |

Biological Activity

The compounds according to the invention underwent pharmacological trials to determine their analgesic effect.

Tests consisting in measuring the in vivo activity of the compounds of the invention on a nociceptive reflex response were performed. In this approach, the latency of the animal's nociceptive reflex response is measured as a pain indicator.

"Tail-Flick" Test

Procedure

The analgesic activity was determined by means of the "tail-flick" test in male Swiss mice (Iffa Credo). This test is based on the spontaneous nociceptive reflex of removal of the

TABLE 2

| No. | Compound (R1 type of anomer concerned) | % MPE max (dose, mg/kg, sc) | ED$_{50}$ 60 min. post-administration, mg/kg | Duration of action, minutes (dose, mg/kg, sc) |
|---|---|---|---|---|
| 1 | (tetrazole α/β) | 50 (10) | 10 | >120 (10) |
| 2 | (tetrazole β) | 100 (1.25) | <1.25 | >120 (1.25) |
| 3 | (2-methyl-1,3,4-oxadiazole α/β) | 100 (5) | 3.2 | >120 (5) |

TABLE 2-continued

| No. | Compound (R1 type of anomer concerned) | % MPE max (dose, mg/kg, sc) | ED$_{50}$ 60 min. post-administration, mg/kg | Duration of action, minutes (dose, mg/kg, sc) |
|---|---|---|---|---|
| 4 | (2-methyl-1,3,4-oxadiazole α) | 65 (10) | 8 | 90 (10) |
| 5 | (2-methyl-1,3,4-oxadiazole β) | 100 (1.25) | <1.25 | >120 (1.25) |
| 6 | (5-(4-methoxyphenyl)-4-(2,2,2-trifluoroethyl)-1,2,4-triazole β) | — | — | — |

The results indicate that the compounds according to the invention have powerful analgesic activities (>50%) for doses of between 1.25 mg/kg and 10 mg/kg if they are administered subcutaneously (measured 60 minutes post-administration) and for doses of between at least 2.5 and 30 mg/kg if they are administered orally (measured 60 minutes post-administration).

These analgesic activities are persistent and long-lasting, for more than 120 minutes after their administration as a single dose.

Among the most active compounds whose activity was evaluated orally, by way of example, compound 5 shows a percentage of maximum analgesic activity (% MPE max index) of 78 for a dose of 10 mg/kg and an ED$_{50}$ at 60 minutes of less than 2.5 mg/kg.

It is thus seen that the compounds according to the invention have analgesic activity.

The compounds according to the invention may thus be used for the preparation of medicaments, in particular medicaments intended for treating or preventing pain.

Thus, according to another of its aspects, a subject of the invention is medicaments comprising a compound of formula (I), or an addition salt thereof with a pharmaceutically acceptable acid, or alternatively a hydrate or a solvate.

These medicaments find their therapeutic use especially in the treatment and prevention of acute or chronic pain, especially peripheral pain or pain associated with inflammatory diseases such as arthritis, rheumatoid arthritis, osteoarthritis, spondylitis, gout, vasculitis, Crohn's disease and irritable bowel syndrome, neuropathic, muscular, bone, post-operative or migraine-related pain, lumbar pain, and cancer-related, diabetes-related or AIDS-related pain.

The compounds according to the invention also find their use in the treatment of sexual dysfunctions and in particular in the treatment of male premature ejaculation, for which the activity of a compound of antalgic type has been shown.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a hydrate or a solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal, rectal or intraocular administration, the active principle of formula (I) above, or the possible salt, solvate or hydrate thereof, may be administered in a unit administration form, as a mixture with standard pharmaceutical excipients, to man and animals for the treatment of the above disorders or diseases.

The appropriate unit forms of administration include oral forms such as tablets, soft or hard gel capsules, powders, granules and oral solutions or suspensions, sublingual, buccal, intratracheal, intraocular, intranasal and inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:

1. A compound of formula (I):

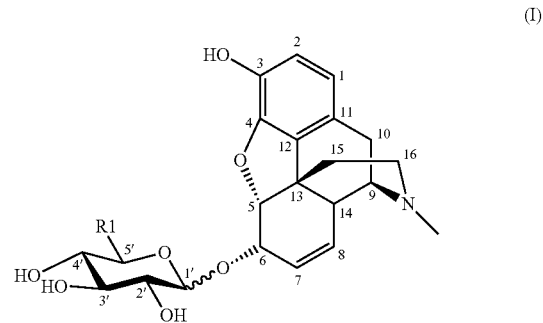

(I)

wherein:
R1 is a 5-membered aromatic heterocyclic group optionally substituted with one or more substituents chosen from halogen atoms and groups ($C_1$-$C_4$)alkyl, halogen, hydroxyl, oxo, halo($C_1$-$C_4$)alkyl, halo($C_1$-$C_4$)alkyloxy, ($C_1$-$C_4$)alkyloxy, aryl($C_1$-$C_4$)alkyl and aryl, the said aryl group being optionally substituted with one or more groups chosen from the groups ($C_1$-$C_4$)alkyl, halo($C_1$-$C_4$)alkyl, hydroxyl and ($C_1$-$C_4$)alkyloxy, or an acid-addition salt, a hydrate or a solvate thereof.

2. The compound of formula (I) according to claim 1, wherein said compound has one or more of the following characteristics:
the aromatic heterocyclic group is chosen from pyrrole, furan, thiophene, imidazole, triazole, tetrazole, oxazole, isoxazole, oxadiazole, thiazole, isothiazole and thiadiazole groups, and
when the aromatic heterocyclic group is substituted with one or more groups, the group is chosen from methyl, ethyl, propyl, isopropyl, butyl, isobutyl, tert-butyl, fluoromethyl, difluoromethyl, trifluoromethyl, chloromethyl, dichloromethyl, trichloromethyl, fluoroethyl, difluoroethyl, trifluoroethyl, chloroethyl, dichloroethyl, trichloroethyl, methoxyphenyl, ethoxyphenyl, propoxyphenyl and butyloxyphenyl groups, or an acid-addition salt, a hydrate or a solvate thereof.

3. The compound of formula (I) according to claim 1, wherein:
the said aromatic heterocyclic group is chosen from tetrazole, triazole and oxadiazole groups, and
when the said aromatic heterocyclic group is substituted with one or more groups, the said group is chosen from methyl, trifluoroethyl and p-methoxyphenyl groups;
or an acid-addition salt, a hydrate or a solvate thereof.

4. The compound of formula (I) according claim 1, selected from the group consisting of:
morphin-6-yl 5-C-(tetrazol-5-yl)-α/β-D-xylopyranoside (1/1);
morphin-6-yl 5-C-(tetrazol-5-yl)-β-D-xylopyranoside;
morphin-6-yl 5-C-(2-methyl-1,3,4-oxadiazol-5-yl)-α/β-D-xylopyranoside (2/3);
morphin-6-yl 5-C-(2-methyl-1,3,4-oxadiazol-5-yl)-α-D-xylopyranoside;
morphin-6-yl 5-C-(2-methyl-1,3,4-oxadiazol-5-yl)-β-D-xylopyranoside; and
morphin-6-yl 5-C-[5-(4-methoxyphenyl)-4-(2,2,2-trifluoroethyl)-4H-1,2,4-triazol-3-yl]-β-D-xylopyranoside;
or an acid-addition salt, a hydrate or a solvate thereof.

5. A pharmaceutical composition comprising a compound of formula (I) according to claim 1, or a pharmaceutically acceptable salt, hydrate or solvate of said compound, and also one or more pharmaceutically acceptable excipient.

6. A pharmaceutical composition comprising a compound of formula (I) according to claim 2, or a pharmaceutically acceptable salt, hydrate or solvate of this compound, and also one or more pharmaceutically acceptable excipient.

7. A pharmaceutical composition comprising a compound of formula (I) according to claim 3, or a pharmaceutically acceptable salt, hydrate or solvate of said compound, and also one or more pharmaceutically acceptable excipient.

8. A pharmaceutical composition comprising a compound of formula (I) according to claim 4, or a pharmaceutically acceptable salt, hydrate or solvate of said compound, and also one or more pharmaceutically acceptable excipient.

9. A method for treating pain in a patient comprising administering to said patient an effective dose of a compound of formula (I) according to claim 1 or a pharmaceutically acceptable salt, hydrate or solvate of said compound.

10. A method for treating pain in a patient comprising administering to said patient an effective dose of a compound of formula (I) according to claim 2 or a pharmaceutically acceptable salt, hydrate or solvate of said compound.

11. A method for treating pain in a patient comprising administering to said patient an effective dose of a compound of formula (I) according to claim 3 or a pharmaceutically acceptable salt, hydrate or solvate of said compound.

12. A method for treating pain in a patient comprising administering to said patient an effective dose of a compound of formula (I) according to claim 4 or a pharmaceutically acceptable salt, hydrate or solvate of said compound.

13. A compound of formula (III):

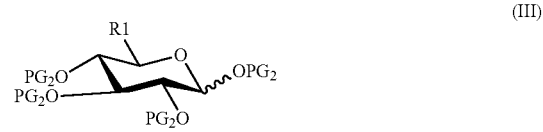

(III)

wherein:
R1 as defined in claim 1, and
PG$_2$ represents a benzoyl group.

14. The compound of formula (III) according to claim 13, wherein R1 is chosen from tetrazole, 1,2,3,4-tetra-O-benzoyl-5-C-2-(4-methoxybenzyl)-2H-tetrazole, 1,2,3,4-tetra-O-benzoyl-5-C-1-(4-methoxybenzyl)-1H-tetrazole and 5-(4-methoxyphenyl)-4-(2,2,2-trifluoroethyl)-1,2,4-triazole groups.

15. A compound of formula (IV):

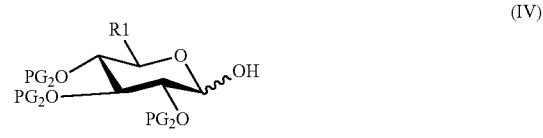

(IV)

wherein:
R1 as defined in claim 1, and
PG$_2$ represents a benzoyl group.

16. The compound of formula (IV) according to claim 15, wherein R1 is chosen from 1,2,3,4-tetra-O-benzoyl-5-C-2-(4-methoxybenzyl)-2H-tetrazole, 1,2,3,4-tetra-O-benzoyl-5-C-1-(4-methoxybenzyl)-1H-tetrazole and 5-(4-methoxyphenyl)-4-(2,2,2-trifluoroethyl)-1,2,4-triazole groups.

17. A compound of formula (V):

(V)

wherein:
R1 as defined in claim 1,
PG$_2$ represents a benzoyl group, and
LG represents a trichloroacetimidate group.

18. The compound of formula (V) according to claim 17, wherein R1 is chosen from 1,2,3,4-tetra-O-benzoyl-5-C-2-(4-methoxybenzyl)-2H-tetrazole, 1,2,3,4-tetra-O-benzoyl-5-C-1-(4-methoxybenzyl)-1H-tetrazole and 5-(4-methoxyphenyl)-4-(2,2,2-trifluoroethyl)-1,2,4-triazole groups.

* * * * *